(12) United States Patent
Quinn et al.

(10) Patent No.: US 10,709,317 B2
(45) Date of Patent: Jul. 14, 2020

(54) CLAMP ASSEMBLY FOR DISPOSABLE ENDOSCOPIC SHEATHS

(71) Applicant: PraesidioDyne, LLC, Indianapolis, IN (US)

(72) Inventors: Brad Hayden Quinn, Indianapolis, IN (US); Bradley Allen Wheeler, Martinsville, IN (US); Kuan Yew Ooi, Penang (MY)

(73) Assignee: PRAESIDIODYNE, LLC, Indianapolis, IN (US)

( * ) Notice: Subject to any disclaimer, the term of this patent is extended or adjusted under 35 U.S.C. 154(b) by 84 days.

(21) Appl. No.: 16/152,310

(22) Filed: Oct. 4, 2018

(65) Prior Publication Data

US 2020/0107703 A1    Apr. 9, 2020

(51) Int. Cl.
| | | |
|---|---|---|
| *A61B 1/00* | (2006.01) | |
| *A61B 17/00* | (2006.01) | |
| *A61B 1/018* | (2006.01) | |
| *A61B 46/17* | (2016.01) | |
| *F16B 2/10* | (2006.01) | |

(52) U.S. Cl.
CPC ........ *A61B 1/00142* (2013.01); *A61B 1/0014* (2013.01); *A61B 1/00135* (2013.01); *A61B 1/00137* (2013.01); *A61B 17/00234* (2013.01); *A61B 1/018* (2013.01); *A61B 46/17* (2016.02);
(Continued)

(58) Field of Classification Search
CPC ............ A61B 1/00142; A61B 1/00144; A61B 1/00135; A61B 1/00137; A61B 1/0014; A61B 2017/00336; A61B 46/10; A61B 46/13; A61B 46/17; A61B 46/40;
(Continued)

(56) References Cited

U.S. PATENT DOCUMENTS

| 10,635 A | * | 3/1854 | Haskins | .................. D06F 55/02 |
| | | | | 24/501 |
| 2,466,284 A | * | 4/1949 | Stinne | ..................... D06F 55/00 |
| | | | | 24/501 |

(Continued)

FOREIGN PATENT DOCUMENTS

| EP | 0440255 A | 8/1991 |
| EP | 0520743 A | 12/1992 |

(Continued)

*Primary Examiner* — John P Leubecker
(74) *Attorney, Agent, or Firm* — Adsero IP

(57) ABSTRACT

Novel tools and techniques for implementing a clamp assembly for disposable endoscopic sheaths are provided. A system includes a sheath, clamp assembly, and protective cover. The sheath may be configured to receive an instrument. The clamp assembly may include a first member coupled to a second member, wherein the first and second members may be placed in a clamping configuration and an open configuration. In the clamping configuration, the first member and the second member are configured to collapse a lumen of the sheath at a location between the first and second members, and in the open configuration the lumen is not collapsed between the first and second members. The protective cover may include a receiver configured to mate with the clamp assembly and to cause the clamp assembly to maintain the open configuration when the clamp assembly is mated with the receiver.

9 Claims, 6 Drawing Sheets

(52) U.S. Cl.
CPC ....... *A61B 2017/00336* (2013.01); *F16B 2/10* (2013.01)

(58) Field of Classification Search
CPC .......... A61M 25/0138; Y10T 24/44385; Y10T 24/44393; F16B 2/10
See application file for complete search history.

(56) References Cited

U.S. PATENT DOCUMENTS

| | | | | |
|---|---|---|---|---|
| 2,728,359 | A * | 12/1955 | Pfarrwaller | D03D 47/24 139/448 |
| 3,169,527 | A | 2/1965 | Sheridan | |
| 3,712,345 | A * | 1/1973 | Pfarrwaller | D03J 5/06 139/196.2 |
| 3,809,072 | A * | 5/1974 | Ersek | A61B 1/00142 600/249 |
| 4,118,270 | A | 10/1978 | Pan et al. | |
| 4,127,293 | A * | 11/1978 | Moreno | E05B 65/1033 292/251 |
| 4,470,407 | A | 9/1984 | Hussein | |
| 4,473,369 | A * | 9/1984 | Lueders | A61M 39/1011 285/419 |
| 4,646,722 | A | 3/1987 | Silverstein et al. | |
| 4,757,381 | A * | 7/1988 | Cooper | A61B 1/00091 206/369 |
| 4,809,678 | A | 3/1989 | Klein | |
| 4,825,850 | A | 5/1989 | Opie et al. | |
| 4,852,551 | A | 8/1989 | Opie et al. | |
| 4,869,238 | A | 9/1989 | Opie et al. | |
| 4,907,395 | A | 3/1990 | Opie et al. | |
| 4,974,580 | A | 12/1990 | Anapliotis | |
| 4,991,565 | A | 2/1991 | Takahashi et al. | |
| 5,063,645 | A * | 11/1991 | Crespo | D06F 55/02 24/501 |
| 5,078,483 | A * | 1/1992 | Herzberg | A61B 1/00142 359/510 |
| 5,168,863 | A * | 12/1992 | Kurtzer | A61B 1/00142 206/363 |
| 5,237,984 | A * | 8/1993 | Williams, III | A61B 1/00142 600/124 |
| 5,267,374 | A * | 12/1993 | Drake | B65D 33/1675 24/30.5 R |
| 5,337,734 | A | 8/1994 | Saab | |
| 5,347,990 | A | 9/1994 | Ebling et al. | |
| 5,415,157 | A * | 5/1995 | Welcome | A61B 46/10 206/571 |
| 5,419,310 | A | 5/1995 | Frassica et al. | |
| 5,429,118 | A | 7/1995 | Cole et al. | |
| 5,514,074 | A | 5/1996 | Yabe et al. | |
| 5,520,607 | A * | 5/1996 | Frassica | A61B 1/00142 248/56 |
| 5,667,068 | A | 9/1997 | Weaver | |
| 5,685,822 | A | 11/1997 | Harhen | |
| 5,813,113 | A * | 9/1998 | Stewart | H01L 25/50 257/E21.705 |
| 5,893,712 | A * | 4/1999 | Stone | A61C 19/04 433/116 |
| 6,086,530 | A | 7/2000 | Mack | |
| 6,293,907 | B1 | 9/2001 | Axon et al. | |
| 6,350,231 | B1 | 2/2002 | Ailinger et al. | |
| 6,350,232 | B1 | 2/2002 | Hascoet et al. | |
| 6,402,511 | B1 * | 6/2002 | Calderwood | A61B 1/00142 433/116 |
| 6,530,881 | B1 * | 3/2003 | Ailinger | A61B 1/00142 600/114 |
| 6,537,205 | B1 | 3/2003 | Smith | |
| 6,579,582 | B1 | 6/2003 | Harhen et al. | |
| 6,599,238 | B2 | 7/2003 | Ooshima et al. | |
| 6,733,440 | B2 | 5/2004 | Ailinger et al. | |
| 6,863,651 | B2 | 3/2005 | Remijan et al. | |
| 6,911,005 | B2 | 6/2005 | Ouchi et al. | |
| 6,921,362 | B2 * | 7/2005 | Ouchi | A61B 1/00142 600/121 |
| 7,062,135 | B2 | 6/2006 | Caracci et al. | |
| D533,662 | S | 12/2006 | Nakajima et al. | |
| 7,238,145 | B2 * | 7/2007 | Robbins | A63B 21/0004 482/11 |
| 9,585,547 | B2 | 3/2017 | Cheng et al. | |
| 2003/0083548 | A1 * | 5/2003 | Ouchi | A61B 1/00142 600/121 |
| 2005/0049460 | A1 | 3/2005 | Mikkaichi | |
| 2005/0143625 | A1 * | 6/2005 | Whitmore, III | A61B 1/00142 600/121 |
| 2005/0197595 | A1 | 9/2005 | Huang et al. | |
| 2006/0052750 | A1 | 3/2006 | Lenker et al. | |
| 2006/0074274 | A1 | 4/2006 | Friedman | |
| 2006/0258906 | A1 * | 11/2006 | Binmoeller | A61B 1/00135 600/114 |
| 2007/0066869 | A1 * | 3/2007 | Hoffman | A61B 1/00135 600/121 |
| 2007/0185383 | A1 | 8/2007 | Mulhern et al. | |
| 2009/0043165 | A1 * | 2/2009 | Kucklick | A61M 25/0662 600/125 |
| 2010/0191050 | A1 * | 7/2010 | Zwolinski | A61B 1/018 600/104 |
| 2010/0249510 | A1 | 9/2010 | Yamada | |
| 2011/0045222 | A1 * | 2/2011 | Peters | C08L 67/02 428/35.8 |
| 2011/0130629 | A1 | 6/2011 | Watanabe et al. | |
| 2011/0152617 | A1 | 6/2011 | Iwamizu et al. | |
| 2011/0282152 | A1 * | 11/2011 | Cant | A61B 1/00096 600/125 |
| 2013/0172840 | A1 * | 7/2013 | Lampotang | A61M 1/0021 604/328 |
| 2014/0005480 | A1 | 1/2014 | Wagner | |
| 2014/0275765 | A1 | 9/2014 | Gebhart et al. | |
| 2016/0022120 | A1 * | 1/2016 | Terliuc | A61B 1/00131 600/124 |
| 2017/0273716 | A1 * | 9/2017 | Garofalo | A61B 17/3423 |
| 2018/0084971 | A1 * | 3/2018 | Truckai | A61B 1/00087 |
| 2019/0231177 | A1 * | 8/2019 | Dreyer | A61B 1/00142 |
| 2019/0246881 | A1 * | 8/2019 | Aull | A61B 1/018 |

FOREIGN PATENT DOCUMENTS

| | | |
|---|---|---|
| EP | 1148988 B1 | 5/2004 |
| GB | 2336540 A | 10/1999 |
| WO | WO 1994/008505 | 4/1994 |
| WO | WO 1994/022358 | 10/1994 |
| WO | WO 1996/027322 | 9/1996 |
| WO | WO 2009/037428 | 3/2009 |

* cited by examiner

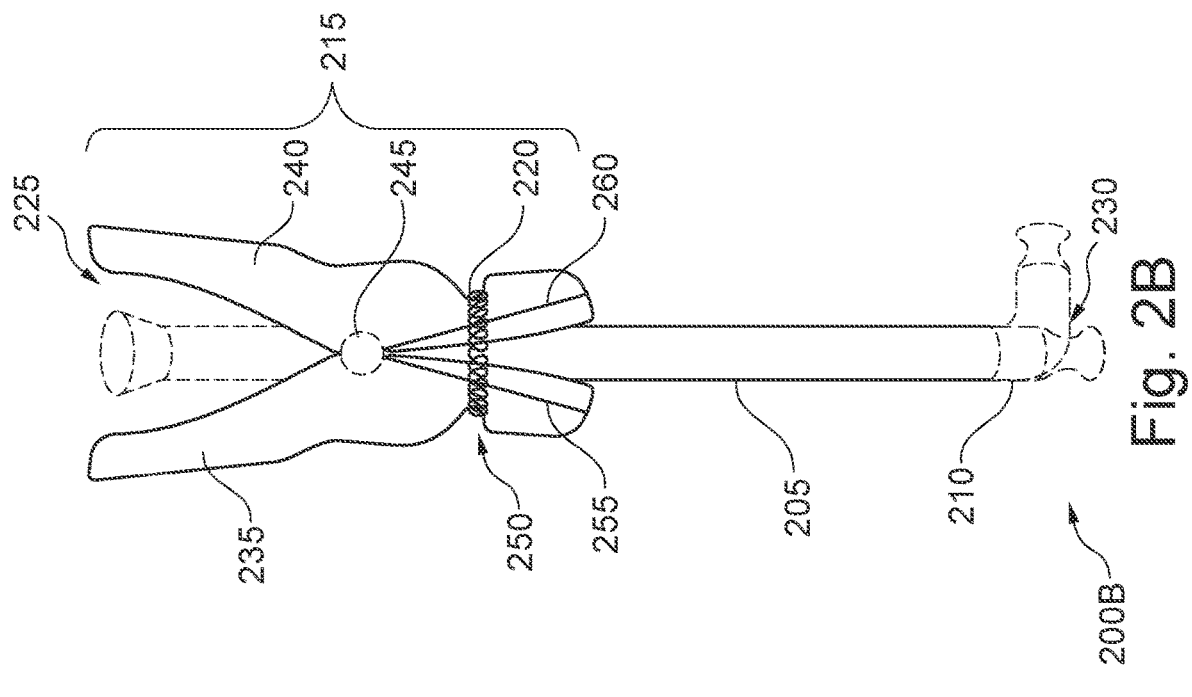
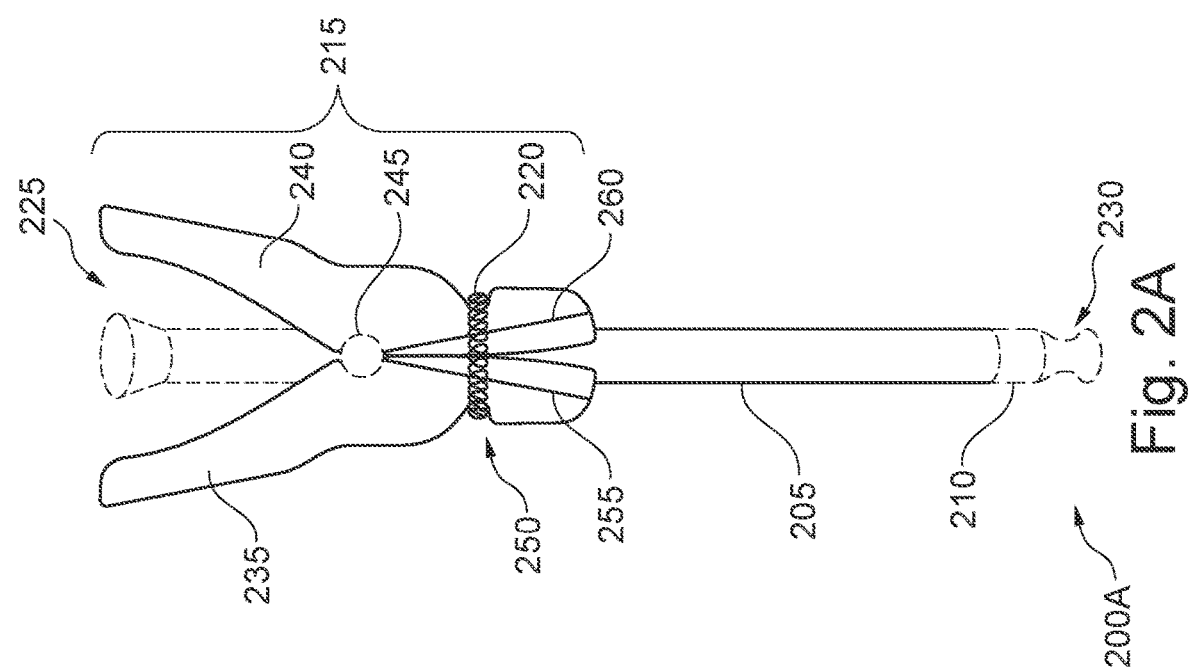

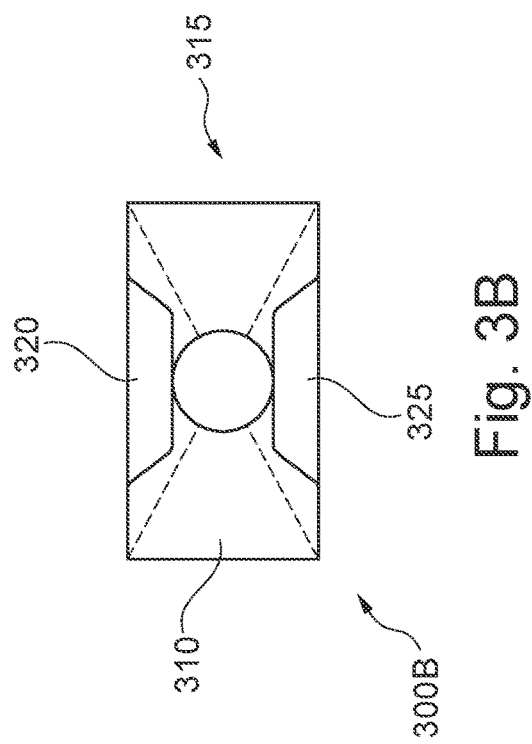
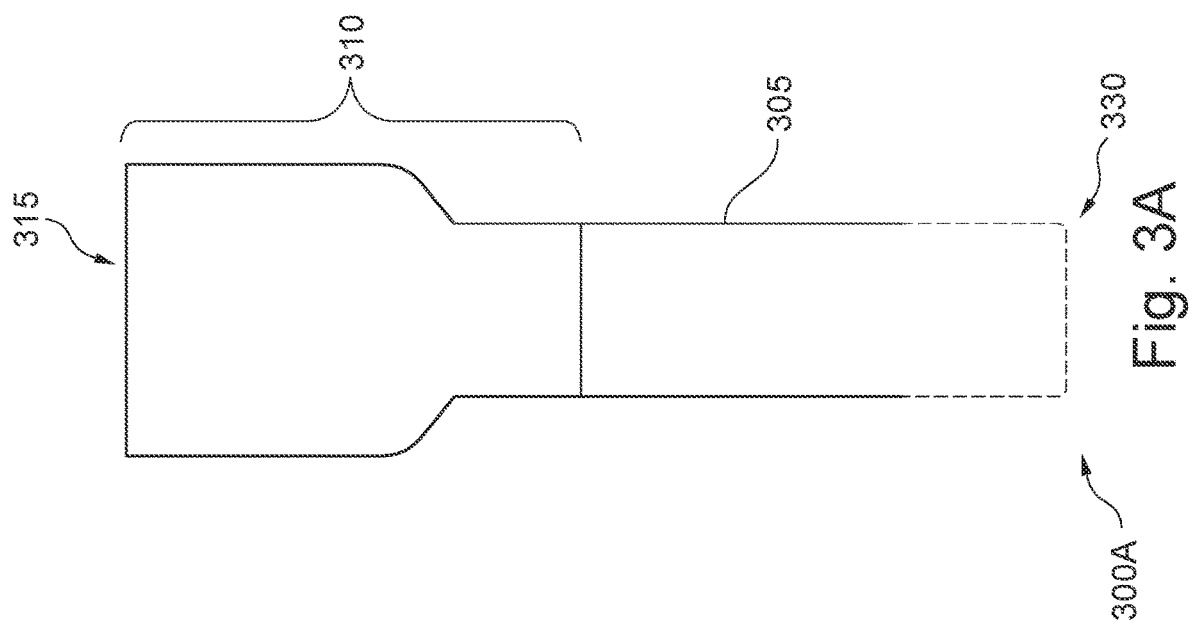

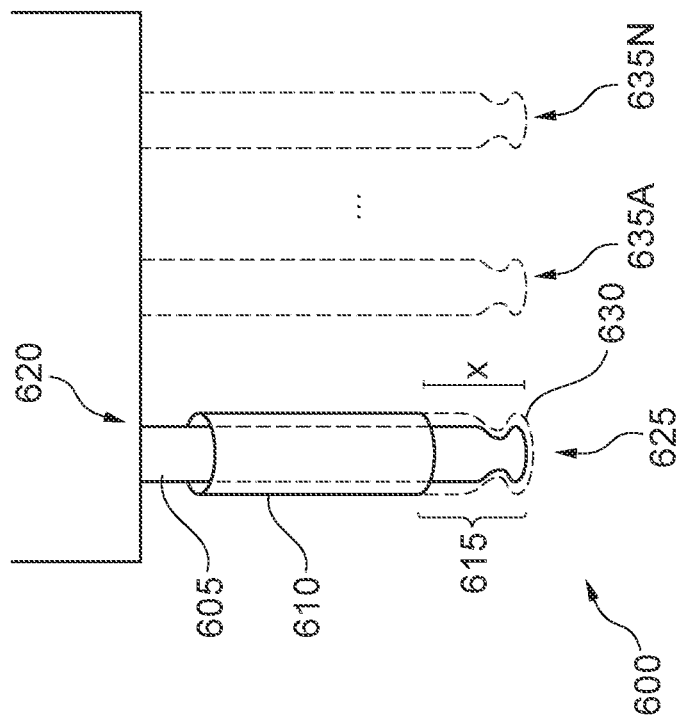
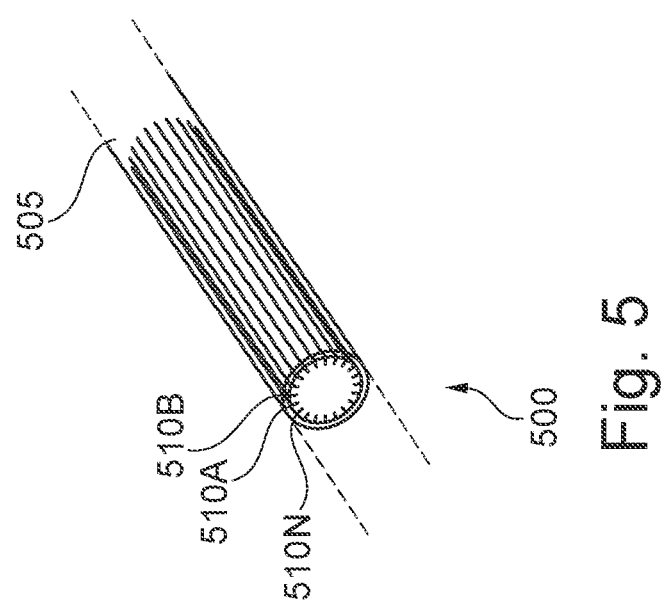

CLAMP ASSEMBLY FOR DISPOSABLE ENDOSCOPIC SHEATHS

CROSS REFERENCE TO RELATED APPLICATIONS

This application may be related to U.S. patent application Ser. No. 16/152,298 filed Oct. 4, 2018 by Brad Quinn et al., entitled "DIP MOLDED DISPOSABLE ENDOSCOPIC SHEATHS," the disclosures of which are incorporated herein by reference in its entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to endoscopic sheaths, and more particularly to a clamp assembly for the preparation and use of disposable endoscopic sheaths.

BACKGROUND

Traditionally, endoscopic probes are reusable items which are sterilized between use in different patients. Sterilization techniques rely on the use of disinfectants, germicides, or other sterilization solutions. Conventional sterilization techniques, however, may become ineffective under various circumstances. For example, as an endoscopic probe wears from repeated use, scratches, cracks, pores, and crevices may trap pathogens and other microbes, preventing the effective sterilization of the probes. Moreover, with repeated exposure to sterilization solutions, drug-resistant bacteria may also continue to survive and propagate on the endoscopic probe.

Conventional endoscopic sheaths have been developed to protect the endoscopic probes and to quickly move between patients. Endoscopic scope sheaths are made to be soft, pliable, and elastic, but also to be as thin as possible to improve clarity. Conventional endoscopic scopes are typically produced, for example, through a thermoforming or injection molding process. Typically, an end cap (also referred to as a lens) are produced separately, and are glued onto a sleeve portion of the sheath. Thus, in conventional sheaths, failures often occur at the locations where the end cap is glued to the sleeve, such that the end cap may tear, or altogether detach from the sleeve. Moreover, typical thermoforming and injection molding processes are limited in the thinness and clarity that may be obtained, and the types of materials that may be used for the sleeve and end cap portions of conventional endoscopic sheaths.

Moreover, care must be taken to maintain the sterility of endoscopic sheaths during transport, and while inserting one or more endoscopic instruments into the sheath. For example, protective covers may be used to prevent the endoscopic sheath from being exposed to pathogens in the air, or from coming into contact with non-sterile surfaces. Typically, medical service providers require assistance (either from another medical service provider or other tool) to remove the sheath from the cover and to insert the one or more endoscopic instruments into the sheath.

Accordingly, novel tools and techniques are described herein to overcome one or more of the problems discussed above.

BRIEF DESCRIPTION OF THE DRAWINGS

A further understanding of the nature and advantages of the embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIG. 2A is a front elevation view of an embodiment of the endoscopic sheath and clamp assembly in a clamping configuration;

FIG. 2B is a front elevation view of the endoscopic sheath and clamp assembly in an open configuration;

FIG. 3A is a front elevation view of an embodiment of a protective cover and receiver;

FIG. 3B is a top plan view of the receiver of the protective cover;

FIG. 5 is a cutaway view of one embodiment of the endoscopic sheath;

FIG. 6 is a schematic diagram of an embodiment of a dip molding system for producing an endoscopic sheath.

DETAILED DESCRIPTION OF CERTAIN EMBODIMENTS

Figure 1:
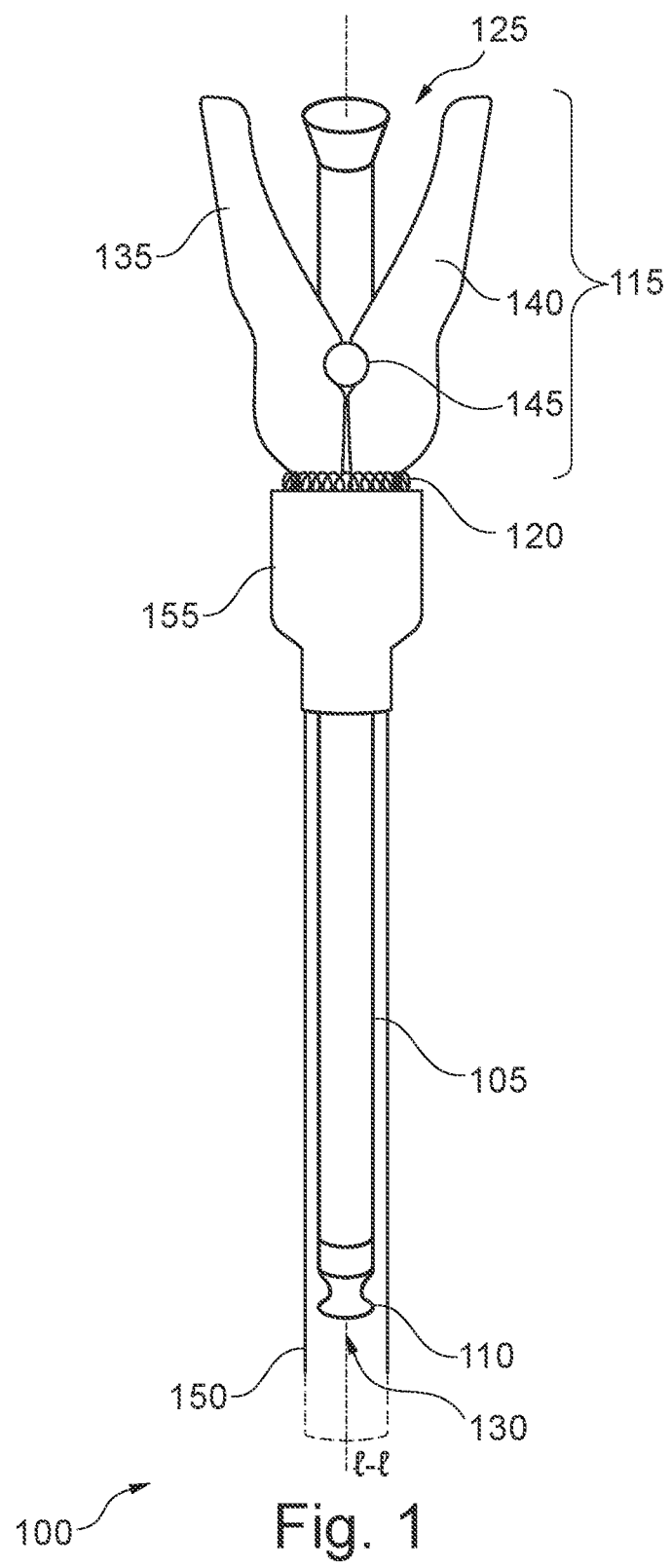
FIG. 1 is a front elevation view of an embodiment of the endoscopic sheath system.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

In an aspect, a system is provided, which may include a sheath, clamp assembly, and protective cover. The sheath may include an elongated body having a first transverse cross-sectional area, the sheath comprising a proximal end and a distal end, the sheath being configured to receive an instrument at the proximal end. The clamp assembly may be coupled to the sheath. The clamp assembly may include a first member coupled to a second member, wherein the first and second members may be placed in a clamping configuration and an open configuration. In the clamping configuration, the first member and the second member may be configured to collapse a lumen defined by the elongated body of the sheath at a location between the first and second members. In the open configuration, the lumen is not collapsed between the first and second members. The protective cover may be configured to receive the sheath. The protective cover may include an elongated body having a second transverse cross-sectional area greater than the first transverse cross-sectional area of the sheath. The protective cover may further include a receiver. The receiver may be configured to mate with the clamp assembly when the sheath is inserted into the protective cover. The receiver may be configured to cause the clamp assembly to maintain the open configuration when the clamp assembly is mated with the receiver.

In another aspect, an apparatus is provided, which may include a clamp assembly. The clamp assembly may include a first member coupled to a second member, wherein the first and second member may be placed in a clamping configuration and an open configuration. The clamp assembly may be configured to couple to a sheath. IN the clamping configuration, the first member and the second member may be configured to collapse a lumen defined by an elongated body of the sheath at a location between the first and second members. In the open configuration, the lumen is not collapsed between the first and second members. The clamp assembly may be configured to be in the open configuration and to remain normally open when the clamp assembly is mated to a receiver. The clamp assembly may further be configured to be in the clamping configuration when the clamp is removed from the receiver.

In a further aspect, an apparatus is provided, which may include a protective cover configured to receive a sheath. The protective cover may include an elongated body having a transverse cross-sectional area greater than a transverse cross-sectional area of the sheath. The protective cover may further comprise a receiver, wherein the receiver may be configured to mate with a clamp assembly of the sheath when the sheath is inserted into the protective cover. The receiver may further be configured to cause the clamp assembly to maintain an open configuration when the clamp assembly is mated with the receiver.

Various modifications and additions can be made to the embodiments discussed without departing from the scope of the invention. For example, while the embodiments described above refer to specific features, the scope of this invention also includes embodiments having different combination of features and embodiments that do not include all the above described features.

FIG. 1 is a front elevation view of an embodiment of the endoscopic sheath system 100. The system 100 includes a sheath 105 having a proximal end 125 and distal end 130, cap 110, clamp assembly 115 comprising a first member 135 and second member 140, spring 120, hinge 145, protective cover 150, and receiver 155. It should be noted that the various components of the system 100 are schematically illustrated in FIG. 1, and that modifications to the system 100 may be possible in different embodiments.

The sheath 105 may include an elongated sheath body extending along longitudinal axis 1-1. The sheath 105 may further include a cap 110 at a distal end 130. The cap 110 may be formed integrally with the elongated body. The cap 110 will be described in greater detail with respect to the embodiments described below. The sheath 105 may further include an opening, at a proximal end 125, configured to receive one or more instruments. In various embodiments, a clamp assembly 115 may be coupled to the sheath 105 at a point between a midpoint of the sheath 105 (e.g., a central point along the longitudinal length of the sheath 205) and the proximal end 125. The clamp assembly 115 may include a first member 135 pivotally coupled to a second member 140 via a hinge 145. The clamp assembly 115 may further include a spring 120 configured to bias the clamp assembly to a clamping position. The clamp assembly 115 may be coupled to a protective cover 150 via a receiver 155 configured to receive the sheath 105 and couple to the clamp assembly 115. The protective cover 150 may have an elongated cover body, also extending along the longitudinal axis 1-1.

In some embodiments, the elongated sheath body may have a circular and/or elliptical cross-sectional shape, defining a lumen between the proximal end 125 and the distal end 130. Accordingly, the elongated body of the sheath 105 may have a tube-like or sleeve-like hollow, cylindrical structure, extending along the longitudinal axis 1-1. In some embodiments, the body of the sheath 105 may define two or more separate lumens between the proximal end 125 and the distal end 130. Thus, the body may be configured to receive one or more instruments in each respective lumen. The body of the protective cover 150 may also include a lumen extending between the proximal end 125 and distal end 130 of the protective cover 150. The body of the protective cover 150 may have a larger cross-sectional area than the body of the sheath 105, such that the sheath 105 can fit within the lumen of the protective cover. Thus, the sheath 105 may be inserted into the protective cover 150 such that the protective cover 150 surrounds at least part of a length of the sheath 105 from the distal end 130, including the cap 110, to a point where the clamp assembly 115 is coupled to the body of the sheath 105. Accordingly, FIG. 1 depicts the sheath 105 and clamp assembly 115 when fully inserted into the protective cover 110 and receiver 155.

In various embodiments, the elongated body of the sheath 105 may comprise, at the proximal end 125, an opening configured to receive one or more instruments. In some embodiments, the opening may be funnel-shaped. The one or more instruments may include, without limitation, endoscopic probes (e.g., ultrasonic probe, camera probe, etc.), fiber optic cameras, lights, and other medical instruments. Accordingly, the body of the sheath 105 may also be configured to hold the one or more instruments within the lumen.

At the distal end 130, the sheath 105 may comprise a cap 110 integrally formed with the body of the sheath. For example, in some embodiments, the sheath 105 may be formed of a polymeric material, such as a thermoplastic or thermoset polymer material. Suitable polymeric materials may include, without limitation, polyvinyl chloride (PVC), polyurethane (PU), polyester, polyamide (e.g., nylon), polycarbonate (PC), polyethylene (PE), polypropylene (PP), polystyrene (PS), acrylonitrile butadiene styrene (ABS), silicone, or a blend of polymeric materials (e.g., polyethylene terephthalate (PET)). The cap 110 may be formed from a common polymer material sharing a common polymeric backbone, such that a polymeric knit is formed between the cap 110 and the body of the sheath 105 where the cap 110 is coupled to the body. Thus, in various embodiments, the cap 110 is a homogeneous part of the sheath 105. In some embodiments, a homogeneous, polymeric knit may be achieved via a dip-molding process, as will be described in greater detail below with respect to FIGS. 6 & 7.

The cap 110 may further be configured to create a hermetic seal with the body of the sheath 105 at the distal end 130. In some embodiments, the cap 110 may be configured to form a hermetic seal around one or more lumens of the sheath 105. In some examples, the body of the sheath may define two or more lumens. Thus, the cap 110 may be configured to be coupled to the body to form a seal around one or more of the two or more lumens. Thus, in some embodiments, one or more endoscopic probes or other medical instruments may be inserted into a lumen that has been sealed by the cap 110, or into a lumen that may remain unsealed by the cap.

The sheath 105, including the cap 110, may exhibit varying degrees of barrier resistance (e.g., permeation resistance of the material to liquids or gases in the ambient surroundings). In some embodiments, a desired barrier resistance of the sheath 105 and/or cap 110 may be achieved by using a blend (e.g., alloy) of polymer materials. In one example, a combination of PVC and PU may be utilized. In further embodiments, barrier enhancement additives may also be used in the sheath 105 and/or the cap 110. In some embodiments, the sheath 105 and/or cap 110 may have a permeation resistance equal to or exceeding (e.g., lower permeability coefficient for various liquids and gases) the permeation resistance of glass. In other embodiments, the sheath 105 and/or cap 110 may have a permeation resistance of the base polymeric material (such as PVC or PU), or any level of permeation resistance between that of the base polymeric material and glass, as determined to be appropriate for the desired application.

In various embodiments, the cap 110 may also be configured to be impedance matched to the operation of an endoscopic probe or other medical instrument. For example, the sheath 105 and/or cap 110 may be configured to be acoustically impedance matched in the operating frequencies of an ultrasonic probe. Accordingly, the sheath 105 and/or cap 110 may be configured to allow acoustic frequencies from the ultrasonic probe to be transmitted through the sheath 105 and/or cap 110, and into the surrounding environment (e.g., tissue, fluid, cavity). Thus, by acoustically impedance matching the acoustic frequencies used by the ultrasonic probe, reflections caused by the sheath 105 and/or cap may be minimized. For example, in some embodiments, an ultrasonic probe with an operating frequency in the range of 2 MHz to 4 GHz may be used for various in vivo applications. Accordingly, the sheath 105 and/or cap 110 may be configured to be acoustically impedance matched with the surrounding tissue, fluid, cavity, or other environment, in the range of 2 MHz to 4 GHz, such that the sheath 105 and/or cap 110 may be configured to reduce acoustic reflections, or in some cases may be acoustically transparent in the range of frequencies involved. In other embodiments, the sheath 105 and/or cap 110 may be acoustically impedance matched to one or more specific frequencies (e.g., 2.5 MHz, 3.5 MHz, 5.0 MHz, 7.5 MHz, 10.0 MHz, 15.0 MHz, or a combination of these frequencies).

Similarly, the sheath 105 and/or cap 110 may be optically impedance matched to the operation of a camera or other optical probe. For example, in the case of a visible light camera, the sheath 105 and/or cap 110 may be configured to maximize optical transparency. In some embodiments, to increase optical transparency, the thickness of the sheath 105 and/or cap 110 may be reduced to be as thin as possible while still maintaining a desired level of structural integrity. In one example, the thickness of the cap 110 may be less than or equal to 500 μm. As previously described with respect to increasing permeation resistance, polymer blending may also be used to improve the optical characteristics of the sheath 105 and/or cap 110. For example, in some embodiments, polymeric materials known to be more optically transparent may be introduced to other polymeric materials used for resilience to physical stresses. In yet further embodiments, the sheath 105 and/or cap 110 may be formed from materials including a polymer additive to improve optical clarity. One such commercially available additive includes, for example, PixClear® manufactured by Pixelligent™. In other embodiments, different types of additives may be added to affect other properties of the sheath 105 and/or cap 110, including, without limitation, flexibility, elasticity, physical resilience, reflectivity (e.g., anti-reflective additives, mirror coatings, etc.), to repel oils, fats, and other lipids (e.g., oleophobic additives), to repel moisture or water (e.g., hydrophobic additives), and to reduce fogging (e.g., anti-fogging agents, hydrophilic additives).

The sheath 105 and/or cap 110 may further be configured to have various elastic properties. For example, the sheath 105 and/or cap 110 may be configured to deform without tearing, ripping, or otherwise compromising its structural integrity. For example, the sheath 105 and/or cap 110 may be configured to be stretched over an endoscopic probe, or become stretched as the endoscopic probe is inserted into the body of a patient. In some embodiments, the sheath 105 may be configured to have a relatively rigid configuration while the cap 110 is configured to have a relatively flexible configuration. In some embodiments, the cap 110 itself may be configured to have a sufficient length to allow the articulation of the cap 110 around the point at which the cap 110 is coupled to the body of the sheath 105. Accordingly, in some examples, the body of the sheath may remain relatively stationary, while an endoscopic probe is manipulated. The cap 110 may be configured to articulate to accommodate the movement of the endoscopic probe within the sheath 105. This will be discussed in greater detail below, with respect to FIG. 2.

In yet further embodiments, the cap 110 may be contoured or otherwise shaped. The shape of the cap 110 may be configured to be adapted to the contours of a tip of an endoscopic probe or other medical instrument. For example, in some embodiments, the tips of an endoscopic probe may have an irregularly shaped contour (for example, a lens element, multi-pronged instrument, hook, scoop, or other irregularly shaped tips). Thus, by configuring the cap 110 to have a contour matching, at least partially, the shape of the tip of the instrument, the surface area in contact between the interior surface of the cap 110 and the surface of the tip of the instrument may be increased. Accordingly, any gaps between an internal surface of the sheath 105 and/or cap 110, which may interfere with the operation of the probe, may be reduced or eliminated. Moreover, by reducing the gaps between the sheath 105 and/or cap 110, and the tip of an instrument, friction between the internal surface of the sheath 105 and/or cap 110, and the tip of the instrument may also be reduced, improving the resilience of the sheath 105 and/or cap 110.

FIGS. 2A & 2B show front elevation views of the endoscopic sheath 205 and clamp assembly 215. FIG. 2A shows a clamping configuration 200A of the endoscopic sheath 205 and clamp assembly 215. FIG. 2B shows an open configuration of the endoscopic sheath and clamp assembly 215. As previously described with respect to FIG. 1, the sheath 205 may include a proximal end 225 and a distal end 230. In various embodiments, the sheath 205 may include, at the distal end 230, a cap 210 formed integrally with the body of the sheath 205. The cap 210 may be contoured or otherwise shaped. In some embodiments, the cap 210 may further be configured to have a sufficient longitudinal length to allow the articulation of the cap 210 around the point at which the cap 210 is coupled to the body of the sheath 205. The cap 210 may be configured to articulate and move to accommodate the movement of the endoscopic probe within the lumen of the sheath 205, as depicted in the clamping configuration 200B. In some embodiments, the cap 210 may be formed of a polymeric material that is, relatively, more flexible and elastic than the body of the sheath 205. Thus, while portions of the sheath 205 above the cap 210 may remain relatively stationary, the cap 210 may be configured to stretch and move with an endoscopic probe or other medical instrument. In some embodiments, the cap 210 may be configured to articulate in any direction relative to the body of the sheath 205. The cap 210 may further be flexible and/or elastic, allowing the probe and/or other instrument to be extended and retracted, while the body of the sheath 205 may remain relatively stationary.

In various embodiments, the clamp assembly 215 may be coupled to the sheath 205 at a location between a midpoint of the sheath 205 and the proximal end 225 of the sheath 205. In further embodiments, the clamp assembly 215 may be coupled to the sheath 205 at any point along its longitudinal length above a minimum operative length of the sheath. The minimum operative length of the sheath may, in some embodiments, correspond to a minimum length of the sheath 205 needed to extend beyond a distal end 230 of the clamp assembly 215 for a particular application. For example, in one embodiment, a minimum operative length of 30 cm may be required to be inserted into a patient for one application.

In various embodiments, the clamp assembly 215 may include a first member 235 and a second member 240. The first member 235 may be coupled to the second member 240 via a hinge 245. A clamping force may be applied to the first member 235 and second member 240 via a spring 220. The spring 220 may, thus, be configured to cause the first and second members 235, 240 to come together, clamping down on the sheath 205 in the clamping configuration 200A. Conversely, in the open configuration 200B, the clamping force of the spring 220 may be overcome to separate the clamping ends 255, 260 of the first and second members 235, 240, allowing the sheath 205 to be opened. For example, in some embodiments, the clamp assembly 215 may be placed in the open configuration by compressing the proximal handles of the first and second members (a portion of the first and second members located on a side of the hinge 245 closest to the proximal end 225). Thus, the clamp assembly 215 may be considered to have a normally closed state when left alone.

In the clamping configuration 200A, the lumen of the sheath 205 may be clamped shut, between the first member 235 and second member 240. For example, the walls of the body of the sheath 205 may be brought into contact, at least locally, by collapsing an inner volume (e.g., the lumen) of the sheath 205. In some embodiments, a hermetic seal may be formed around an area that is clamped by the clamping assembly 215, between the first and second members 235, 240. Thus, pathogens and particulate matter from the surrounding environment may be prevented from entering the lumen of the sheath 205. In the open configuration 200B, the sheath 205 may no longer be forced into contact by the clamping assembly 215, allowing the walls of the sheath 205 to separate and expand, allowing entry (for example, by an endoscopic probe or other medical instrument) into the lumen of the sheath 205. When an endoscopic probe or other medical instrument has been inserted into the lumen of the sheath 205, the clamp assembly 215 may further be configured to apply a clamping force to the one or more endoscopic probes or other instruments within lumen. Thus, the clamp assembly 215 may further be configured to hold the sheath 205 in place over the one or more endoscopic probes and/or other instruments.

In some embodiments, the spring 220 may be an annular spring, extending circumferentially around both the first and second members 235, 240. In other embodiments, other configurations may be utilized. For example, the spring 220 may include, without limitation, tension springs, compression springs (e.g., a metal coil spring), and torsion springs. In some embodiments, the spring 220 may be placed in an internal configuration (e.g., a torsion spring placed around or near the hinge 245).

In various embodiments, the first member 235 may include a first lateral guide 255, and the second member 240 may include a second lateral guide 260. The first and second lateral guides 255, 260 may be configured to couple to the receiver of the protective cover. As the sheath 205 and clamping assembly 215 is pushed into the protective cover, the lateral guides 255, 260 may be configured to cause the first and second members 235, 240 to be separated. For example, as depicted in FIGS. 2A and 2B, the first and second lateral guides 255, 260 may be configured to diverge, from an intersection point at the hinge 245, as it progresses towards the distal end 230. Thus, as the clamp assembly 215 is pushed into a receiver, the receiver may, in turn, act as a wedge, pushing against the first and second lateral guides 255, 260 from the distal end 230 towards the hinge 245 to drive the first and second members 235, 240 apart and into an open configuration 200B. Thus, while sections of the first and second members 235, 240 on a distal side (e.g., side closer to the distal end 225) of the hinge 245 may be driven apart, while the proximal end of the first and second members 235, 240 may be pushed closer together. In other embodiments, the first and second lateral guides 255, 260, may extend substantially parallel to the longitudinal axis of the sheath 205 while still producing a similar effect as the protrusion drives the first and second members 235, 240 apart.

In some embodiments, the first and second lateral guides 255, 260 may be a track, in which the first and second members 235, 240 are contoured and/or the lateral guides 255, 260 are formed as depressions and/or indentations in a lateral surface of the first and second members 235, 240. In other embodiments, other configurations may be used. For example, the lateral guides may be formed as protrusions, such as a flange or other structure, extending out from the lateral surface of the first and second members.

FIGS. 3A & 3B illustrate different views of the protective cover 305 and receiver 310. FIG. 3A illustrates a front elevation view 300A of the protective cover 305 and receiver 310. FIG. 3B illustrates a top-down plan view 300B, looking down into the receiver 310. In various embodiments, the protective cover 305 may include an elongated body, having a proximal end 315 and a distal end 330. The protective cover 305 may be coupled to a receiver 310 at the proximal end 315.

As previously described with respect to FIG. 1, in various embodiments, like the sheath, the body of the protective cover 305 may be an elongated, tube-like or sleeve-like hollow, cylindrical structure. The body of the protective cover 305 may define a lumen extending between the proximal end 315 and distal end 330. The body of the protective cover 305 may be configured to have a larger cross-sectional area than a cross-sectional area of a sheath, such that the sheath can fit within the lumen of the protective cover. In some embodiments, the protective cover 305 may further have a length that is greater than a length of the sheath inserted into the protective cover 305. Thus, the protective cover may enclose the sheath, at least circumferentially, for the entire length of the sheath inserted. In some embodiments, the distal end 330 of the protective cover may be closed off (e.g., hermetically sealed). In some embodiments, the distal end 330 of the protective cover may remain open. The protective cover 305, accordingly, may be configured to shield the enclosed portions of the sheath from coming into contact with any external surfaces, as well as to protect the sheath from coming into contact with pathogens, particulate matter, liquids, droplets, or other foreign materials from the surrounding environment. For example, the protective cover 305 may protect the sheath from unwanted liquids being splashed or sprayed, airborne pathogens and droplets, contact with clothing, hands, skin, walls, equipment, and other unwanted surfaces. In yet further embodiments, the protective cover 305 may further be configured to restrict the movement of the sheath within the protective cover 305, such that the external surface of the sheath does not come into contact with an internal surface of the protective cover 305.

In various embodiments, the elongated body of the protective cover 305 may be coupled to, at the proximal end 315, a receiver 310. The receiver 310 may be configured to include an opening to receive the sheath, and one or more instruments to be inserted into the sheath. As depicted in the top-down plan view, in some embodiments, the opening of the receiver 310 may be funnel-shaped or tapered inwards towards an opening the size and shape of the body of the protective cover 305. The receiver 310 may further be configured to fit, at least partially, the clamp assembly in an open configuration within the opening.

In various embodiments, the receiver 310 may further include one or more protrusions, such as the first protrusion 320, and second protrusion 325 corresponding to first and second lateral guides of the clamp assembly (such as first and second lateral guides 255, 260 of FIGS. 2A & 2B). Accordingly, the first and second protrusions 320 and 325 may be configured to mate with one or more of the lateral guides of the clamp assembly. In some embodiments, as depicted, the first and second protrusions 320, 325 may have a wedge-like shape configured to be accepted between the first and second lateral guides. The first and second protrusions 320, 325 may, thus, be configured to drive the first and second members of the clamp assembly apart as it progresses along the first and second lateral guides towards a hinge of the clamp assembly. In some embodiments, the first and second protrusions 320, 325 may exhibit a taper, widening from the proximal end 315 to the distal end 325. Accordingly, as the first and second protrusions 320, 325 progress along the first and second lateral guides 255, 260, the widening of the first and second protrusions may cause the first member 325 to separate from the second member 240. In further embodiments, instead of the first and second protrusions 320, 325, the receiver 310 may include one or more depressions (not depicted) configured to be mated to one or more lateral guides of the clamp assembly, as previously described. As the lateral guides progress down the one or more depressions of the receiver 310, the first and second members of the clamp assembly may similarly be separated.

Figure 4:
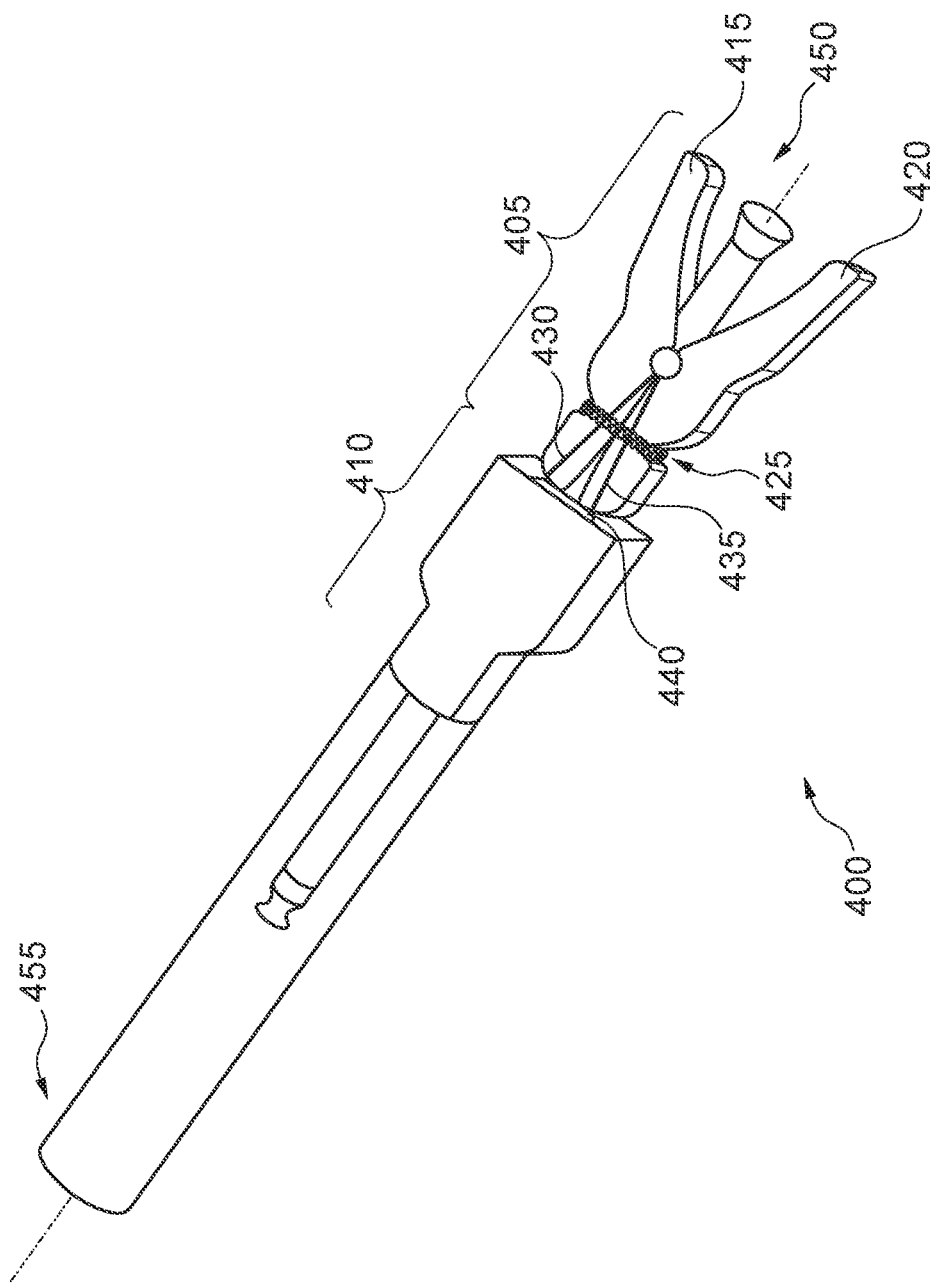
FIG. 4 is a perspective view of the endoscopic sheath system.

FIG. 4 is a perspective view of the endoscopic sheath system 400. As previously described with respect to FIG. 1, the system 400 includes a clamp assembly 405, receiver 410, first member 415, second member 420, spring 425, first lateral guide 430, second lateral guide 435, and a protrusion 440. It should be noted that the various components of the system 400 are schematically illustrated in FIG. 4, and that modifications to the system 400 may be possible in different embodiments.

As depicted, the clamp assembly 405 is being inserted into the receiver 410. The clamp assembly 405 may include a first and second members 415, 420, each respectively including a first and second lateral guides 430, 435. The first and second lateral guides 430, 435 may be configured to couple (e.g., be mated to) the protrusion 440 of the receiver 410. The first and second lateral guides 430, 435 may be configured to diverge, from the hinge of the clamp assembly 405. Thus, as the clamp assembly 405 is pushed into the receiver 410, the protrusion 440 may cause the first and second members 415, 420 to be driven apart on a distal side of the hinge as previously described. Accordingly, the protrusion 440 may be configured to engage both of the first and second lateral guides 430, 430. In further embodiments, the receiver 410 may include a second protrusion (not visible), as described with respect to FIG. 3B. The second protrusion may similarly mate be coupled to additional lateral guides on the other side (not visible) of the clamp assembly 405.

In various embodiments, the sheath and clamp assembly 405, before being engaged to the receiver 410, may be normally closed (e.g., in the clamping configuration). In some examples, the sheath and clamp assembly 405 may be provided to a provider in its packaging, separate from the protective cover. When a provider is ready to insert an endoscopic probe or other instrument into the sheath, the provider may then insert the sheath into the protective cover. By inserting the sheath into the protective cover, the receiver 410 of the protective cover may cause the clamp assembly 405 to have an open configuration, thus allowing entry of endoscopic probe or other instrument into the sheath. Thus, while the clamp assembly 405 is fully mated (e.g., fully inserted) to the receiver 410, the clamp assembly 405 may be considered to be normally open. The sheath and clamp assembly 405 may then remain in the protective cover and receiver 410 while awaiting use or during transport to a patient. When ready to be used, the sheath and clamp assembly 405 may be removed from the protective cover and receiver 410. The clamp assembly 405 may further be configured to apply a clamping force to the one or more endoscopic probes or other instruments within the sheath when removed from the receiver 410. Thus, the clamp assembly 405 may further be configured to hold the sheath in place over the one or more endoscopic probes and/or other instruments.

FIG. 5 is a cutaway view of one embodiment of the endoscopic sheath 500. In some embodiments, the sheath 500 may include a smooth outer surface 505, and patterning within the lumen. For example, the sheath 500 may include a plurality of longitudinal ridges 510A-510N. The longitudinal ridges 510A-510N may be configured to mitigate lateral bending and longitudinal collapsing (e.g., compressing in a longitudinal direction) of the body of the sheath 500. The longitudinal ridges 510A-510N may further be configured to reduce a surface area longitudinally in contact with one or more endoscopic probes and/or other instruments being inserted into and pulled out of the body of the sheath, thus making insertion and removal of the various endoscopic probes and instruments easier. Moreover, the longitudinal ridges may further be configured to create air channels within the body of the tube to prevent vacuums from being formed, and the inner surface of the sheath from becoming attached to the surfaces of an endoscopic probe or other instrument.

FIG. 6 is a schematic diagram of an embodiment of a dip molding system 600 for producing an endoscopic sheath. The system 600 may include a mold 605 having a head 615 of length x, a body 610 of a sheath, cap 630, and one or more additional molds 635A-635N. It should be noted that the various components of the system 600 are schematically illustrated in FIG. 6, and that modifications to the system 600 may be possible in different embodiments.

In various embodiments, the mold 605 may be an elongated structure, such as a mandrel, having a proximal end 620 and distal end 625. The mold 605 may be configured to allow the body 610 of the sheath to be slid over it, exposing a head 615 of the mold 605. Accordingly, in some embodiments, the mold 605 may be configured to have a cross-sectional area to allow the body 610 of the sheath to be slid onto the mold 605 without falling off when inverted. The body 610 of the sheath may be open at both the proximal end 620 and distal end 625.

In various embodiments, the head 615 of the mold 605 may be located at a distal end 625 of the mold 605. The head 615 may have a length x. In various embodiments, the length x of the head 615 may be adjustable to produce caps 630 of varying lengths. For example, to create a longer cap 630, the length of the head 615 may be increased by sliding the body 610 of the sheath higher up on the mold 605 closer to the proximal end 620. Once a desired length x has been created, the mold 605 may be dipped into a polymer bath (not shown), and subsequently removed. The polymer bath may be a heated bath of polymeric materials, as previously described. Suitable polymeric materials may include various thermoplastic and thermoset polymer materials, such as PVC, PU, polyester, polyamide (e.g., nylon), PC, PE, PP, PS, ABS, PET, silicone, as well as blends of polymeric materials.

As the polymeric materials from the polymer bath cure around the head 615 of the mold 605, the cap 630 may be formed over the head 615 of the mold 605. In various embodiments, the polymer bath may include polymeric materials sharing the same polymer backbone as the body 610 of the sheath. For example, for a PVC body, the polymer bath may also utilize PVC. Thus, the cap 630 may be integrally formed with the body 610 of the sheath. Thus, the cap 630 may be formed from a common polymer material sharing a common polymeric backbone, such that a polymeric knit is formed between the cap 630 and the body 610 of the sheath. In this way, the cap 630 may be configured to be a homogeneous part of the sheath.

The cap 630 may further be configured to create a hermetic seal with the body 610 of the sheath. As previously described, the sheath, including the body 610 and cap 630, may exhibit varying degrees of barrier resistance (e.g., permeation resistance). In some embodiments, a desired barrier resistance of the sheath may be achieved by blending (e.g., alloying) two or more different polymers. In one example, a combination of PVC and PU may be utilized as part of the polymer bath. In further embodiments, barrier enhancement additives may be added to the polymer bath, as previously described, to cause the cap 630 to have an increased barrier resistance than a polymeric material (or blend of polymeric materials) would have without the additive.

As previously described with respect to previous embodiments, the longitudinal length of the cap 630, as determined by the length x of the head 615 dipped in the polymer bath, may allow the cap 630 to articulate around the point at which the cap 630 becomes coupled to the body 610. In some embodiments, the cap 630 may be configured to be relatively, more flexible and elastic than the body 610. For example, the body 610 may include a patterning, such as longitudinal ridges (as described with respect to FIG. 5), while the cap may be formed to be as smooth as possible. In other embodiments, the thickness of the cap 630 may be less than the thickness of the body 610. Thus, while the body 610 may remain relatively stationary during bending of an endoscopic probe or other instrument, the cap 630 may be configured to stretch and move with the endoscopic probe or other instrument. In yet further embodiments, a softening additive may be added to the polymer bath. Thus, by controlling the length x, and in some examples, the thickness and/or additives in the polymer bath, the cap 630 may be configured to articulate in any direction relative to the body 610.

In various embodiments, the cap 630 may further be given a contour or otherwise shaped via the head 615 of the mold 605. For example, the head 615 may be configured to have a desired contoured shape for the cap 630. Thus, the head 615 may be configured to impart the contoured shape to the cap 630. In various embodiments, the contoured shape may be configured to match a shape of a tip of an endoscopic probe or other instrument. For example, in some embodiments, the tips of an endoscopic probe may have an irregularly shaped contour (for example, a lens element, multi-pronged instrument, hook, scoop, or other irregularly shaped tips). Thus, by using a mold 605 where the head 615 is configured to have a contour matching, at least partially, the shape of the tip of the instrument, the cap 630 will also be formed to have the same contoured shape.

In various embodiments, it may be desirable to increase or otherwise improve the optical characteristics of the cap 630. Accordingly, in various embodiments, the head 615 of the mold may be a low-grain lens steel, polished to a mirror finish. In this way, the surface irregularities in both the interior and external surfaces of the cap 630 may be reduced. In further embodiments, the head 615 of the mold 605 may be gold-tipped or gold-plated to further reduce surface irregularities that may hinder optical clarity. In yet further embodiments, clarity may be improved by reducing the thickness of the cap 630. In some embodiments, this may be accomplished by controlling the amount of time the mold 605 is placed in the polymer bath, the temperature of the polymer bath, and/or the polymeric materials used in the bath. As previously described, in some embodiments, different blends of polymeric materials may also be used to improve the clarity of the cap 630. In further embodiments, additives may be added to the polymer bath to improve optical clarity, as previously described, to cause the cap 630 to increase optical clarity over a cap produced from the polymeric material (or blend of polymeric materials) without the additive.

In some embodiments, the body 610 may have been formed prior to the cap 630. In some embodiments, the body 610 may be produced using a dip molding process. For example, a mold, such as a mandrel, exhibiting the desired interior features and cross-sectional area for the body 610 may be dipped into a polymer bath and left to cure. In some examples, the same mold 605 may be used to produce the body 610. In some embodiments, the body 610 may be produced to include an internal patterning, such as, without limitation, longitudinal ridges (as described with respect to FIG. 5). Accordingly, the mold used to produce the body 610 may include a plurality of longitudinal depressions corresponding to the plurality of longitudinal ridges. In other embodiments, the body 610 may be produced using a different production process, including, without limitation, injection molding or thermoforming.

Figure 7:
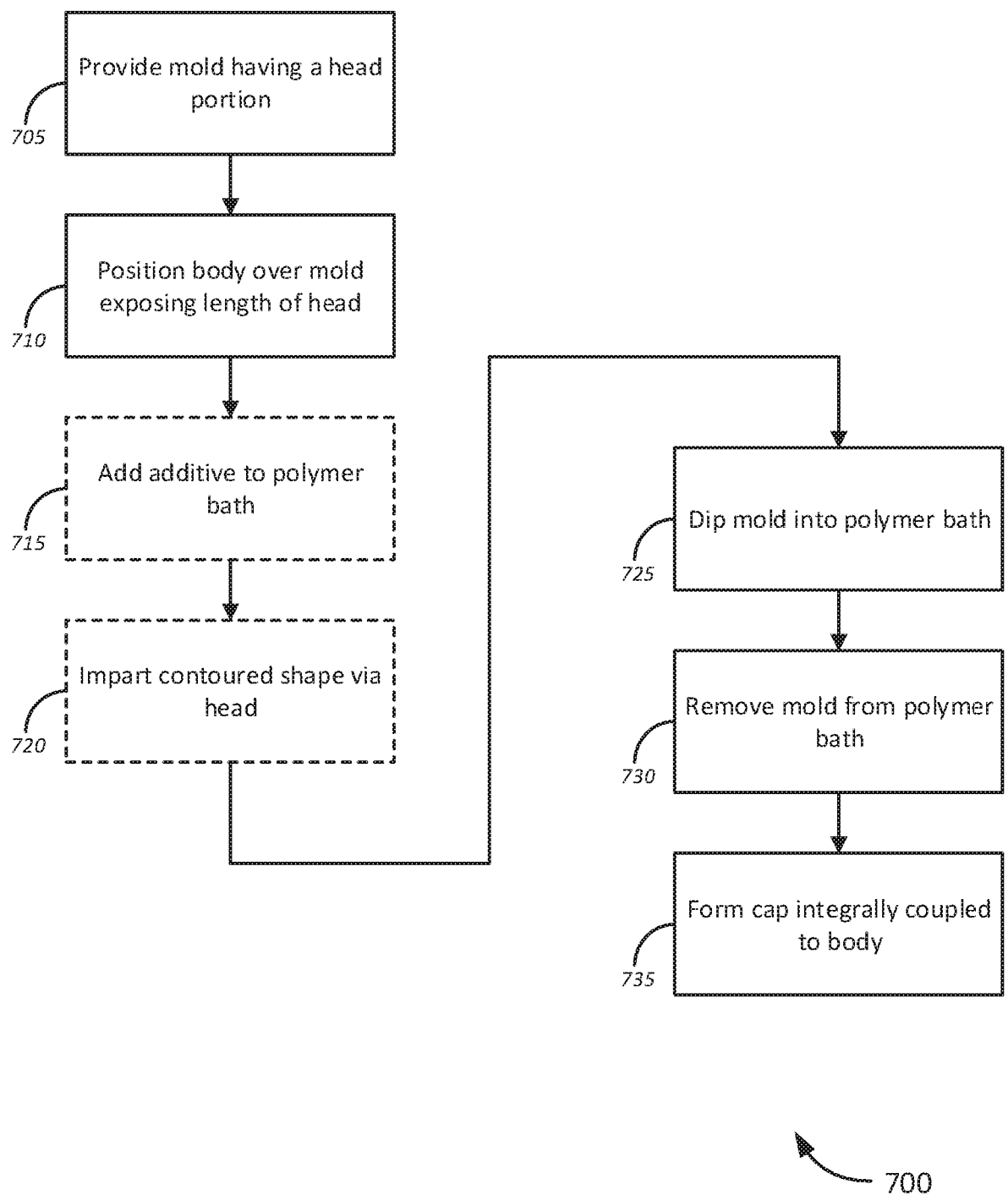
FIG. 7 is a flow diagram of a method for a dip-molding process for producing endoscopic sheaths.

FIG. 7 is a flow diagram of a method 700 a for dip-molding process for producing endoscopic sheaths, in accordance with various embodiments. The method 700 begins, at block 705, by providing a mold comprising a head portion. As previously described with respect to FIG. 6, the mold may be a substantially elongated structure, such as a mandrel, having a proximal end and a distal end. The mold may include a head portion at a distal portion.

At block 710, the method continues by positioning a body of a sheath over the mold, exposing a desired length of the head portion. As previously described, the body of the sheath may have a substantially elongated, hollow shape. The body may be configured to have openings at both the proximal end and the distal end. The body may be positioned over the mold to expose a desired length of the mold. In various embodiments, as previously described, the length of the cap may be adjusted by controlling the exposed length of the head of the mold.

The method 700 continues, at optional block 715, by adding additives to a polymer bath into which the mold will be dipped. As previously described, in some embodiments, barrier enhancement additives may be introduced to the polymer bath to increase the barrier resistance (e.g., permeation resistance) of the polymeric materials used in the polymer bath. In further embodiments, additives may be provided to adjust other characteristics of the polymeric materials, including, without limitation, optical clarity, flexibility, elasticity, physical resilience, reflectivity (e.g., anti-reflective additives, mirror coatings, etc.), to repel oils, fats, and other lipids (e.g., oleophobic additives), to repel moisture or water (e.g., hydrophobic additives), and to reduce fogging (e.g., anti-fogging agents, hydrophilic additives). At optional block 720, a contoured shape may be introduced to the cap via the head portion of the mold. Thus, a mold with a specifically shaped head may be used in various embodiments.

At block 725, the method 700 continues by dipping the mold at least once into one or more polymer bath, which could be only the polymer bath of block 710, 715 or more than the single polymer bath including other baths of different compositions. As previously described, the polymer bath(s) may include one, or a blend of two or more polymeric materials. In some embodiments, polymer blends may be utilized to improve the characteristics of the cap, such as barrier resistance, optical clarity, flexibility, elasticity, and physical resilience over a single constituent polymeric material.

At block 730, the mold may be removed from the polymer bath, and left to cure. The method 700 continues, at block 735, by forming the cap, integrally coupled to the body. As previously described, the polymer bath may include polymeric materials sharing the same polymer backbone as the body of the sheath. By using a common polymer material sharing a common polymeric backbone, such that a polymeric knit is formed between the cap and the body of the sheath, the cap may be formed as integral to and homogeneous with the body of the sheath.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A system comprising:
   a sheath comprising an elongated body having a first transverse cross-sectional area, the sheath comprising a proximal end and a distal end, the sheath being configured to receive an instrument at the proximal end;
   a clamp assembly coupled to the sheath, the clamp assembly comprising a first member coupled to a second member, wherein the first and second members may be placed in a clamping configuration and an open configuration, wherein in the clamping configuration the first member and the second member are configured to collapse a lumen defined by the elongated body of the sheath at a location between the first and second members, and in the open configuration the lumen is not collapsed between the first and second members; and
   a protective cover configured to receive the sheath, the protective cover comprising an elongated body having a second transverse cross-sectional area greater than the first transverse cross-sectional area of the sheath, the protective cover further comprising a receiver,
   wherein the receiver is configured to mate with the clamp assembly when the sheath is inserted into the protective cover,
   wherein the receiver is configured to cause the clamp assembly to maintain the open configuration when the clamp assembly is mated with the receiver.

2. The system of claim 1, wherein the clamp assembly further comprises a spring configured to bias the clamp assembly to the clamping configuration, and to cause the clamp assembly to be normally in the clamping configuration when removed from the receiver.

3. The system of claim 2, wherein the spring is an annular spring positioned circumferentially around the first and second member.

4. The system of claim 1, wherein the clamp assembly further comprises a hinged joint rotatably coupling the first member to the second member, wherein each of the first member and second member are configured to rotate about the hinged joint.

5. The system of claim 1, wherein the first member comprises a first lateral guide, wherein the receiver comprises a protrusion configured to engage the first lateral guide, wherein as the clamp assembly is inserted into the receiver, the first lateral guide is configured to engage the protrusion, wherein the protrusion is configured to separate the first member from the second member as the protrusion travels along the first lateral guide.

6. The system of claim 5, wherein the protrusion is tapered to gradually spread the first member apart from the second member as the protrusion travels along the first lateral guide.

7. The system of claim 5, wherein the second member further comprises a second lateral guide, the protrusion being configured to engage both the first and second lateral guides.

8. The system of claim 1, wherein the sheath comprises a thermoplastic polymer material.

9. The system of claim 1, wherein the protective cover comprises a distal end and a proximal end, wherein the receiver is positioned at the proximal end of the protective cover.

* * * * *